US00PP34905P3

(12) United States Plant Patent
Olesen et al.

(10) Patent No.: US PP34,905 P3
(45) Date of Patent: Jan. 10, 2023

(54) ***CLEMATIS* PLANT NAMED 'EVIPO105'**

(50) Latin Name: *Clematis viticella*
Varietal Denomination: Evipo105

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,630

(22) Filed: Sep. 7, 2021

(65) Prior Publication Data

US 2022/0095516 P1 Mar. 24, 2022

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72
See application file for complete search history.

(56) References Cited

PUBLICATIONS

CPVO Application Consultation Register, *Clematis* plant named, 'EVIPO105', QZ PBR 2020/2278, filed Sep. 21, 2020, downloaded from https://online.plantvarieties.eu/publicConsultationDetails?registerId=20202278&denomination=evipo105.*

* cited by examiner

*Primary Examiner* — Anne Marie Grunberg

(57) ABSTRACT

A new *Clematis* plant with a compact growth habit, profuse, purple-violet flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo105'.

This application claims priority to Plant Breeder's Rights Application Number 2020/2278, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo105' originated as a single seedling from the stated cross.

The new *Clematis* plant may be distinguished from its female seed parent and male pollen parent by the following characteristics. The female seed parent has a flower tepal colour of Purple 75C while the new variety has Violet Group 90C tepals. The male seed parent has medium red tepals while the new variety has purple-violet tepals.

The objective of the hybridization of this *Clematis* plant was to create a new and distinct variety for nursery culture with unique qualities such as:

1. Uniform and abundant purple-violet flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo105' was selected by Mogens N. Olesen and Raymond J. Evison in their *Clematis* development program in the Channel Islands, United Kingdom in 2008. Asexual reproduction of 'Evipo105' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo105' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo105'.

Specifically illustrated in FIG. 1 of the drawings is a flowering stem with leaves and flower buds attached, open flowers viewed from above and underneath, tepals detached, and reproductive flower parts.

Figure 1:
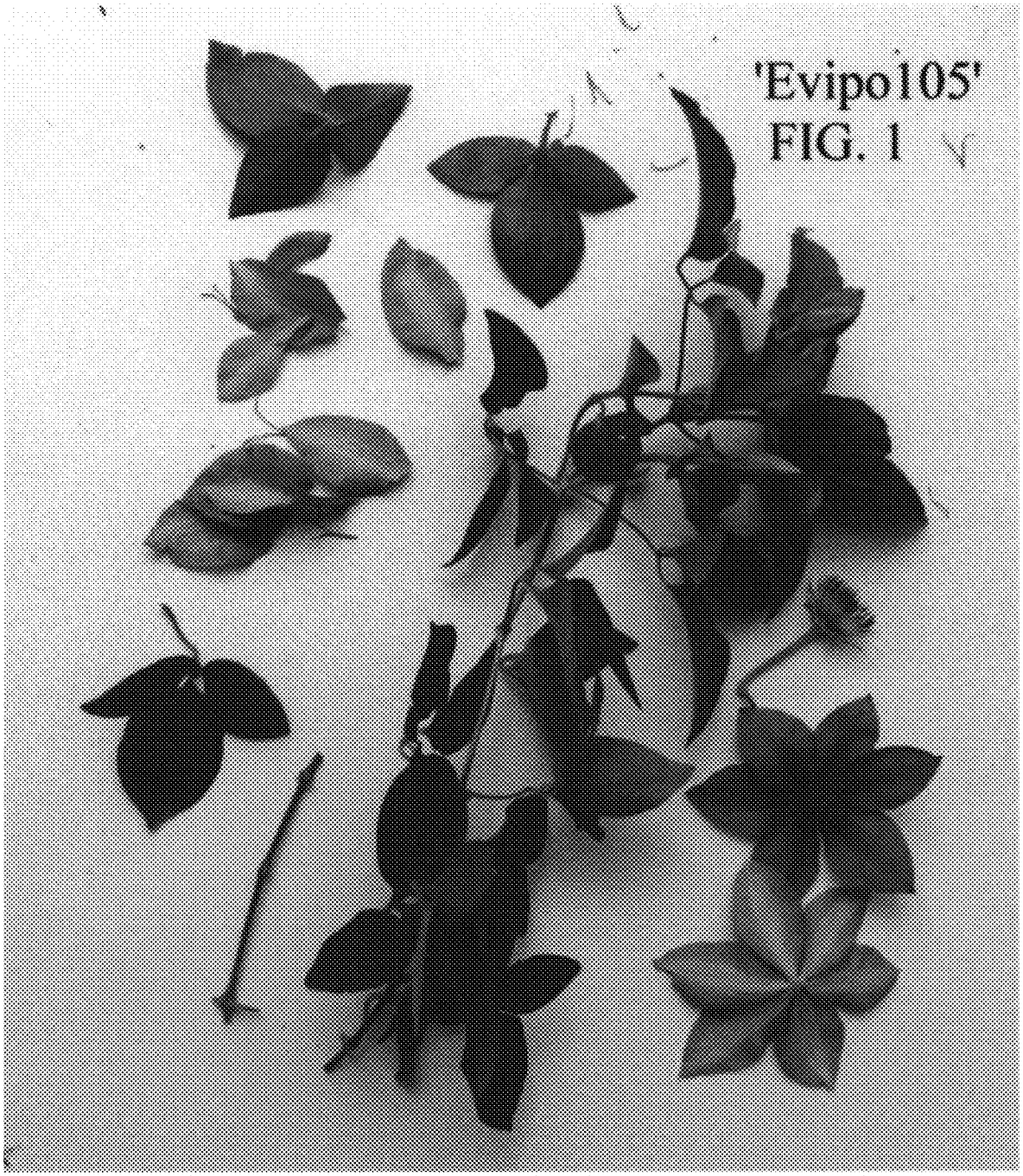
Figure 2:
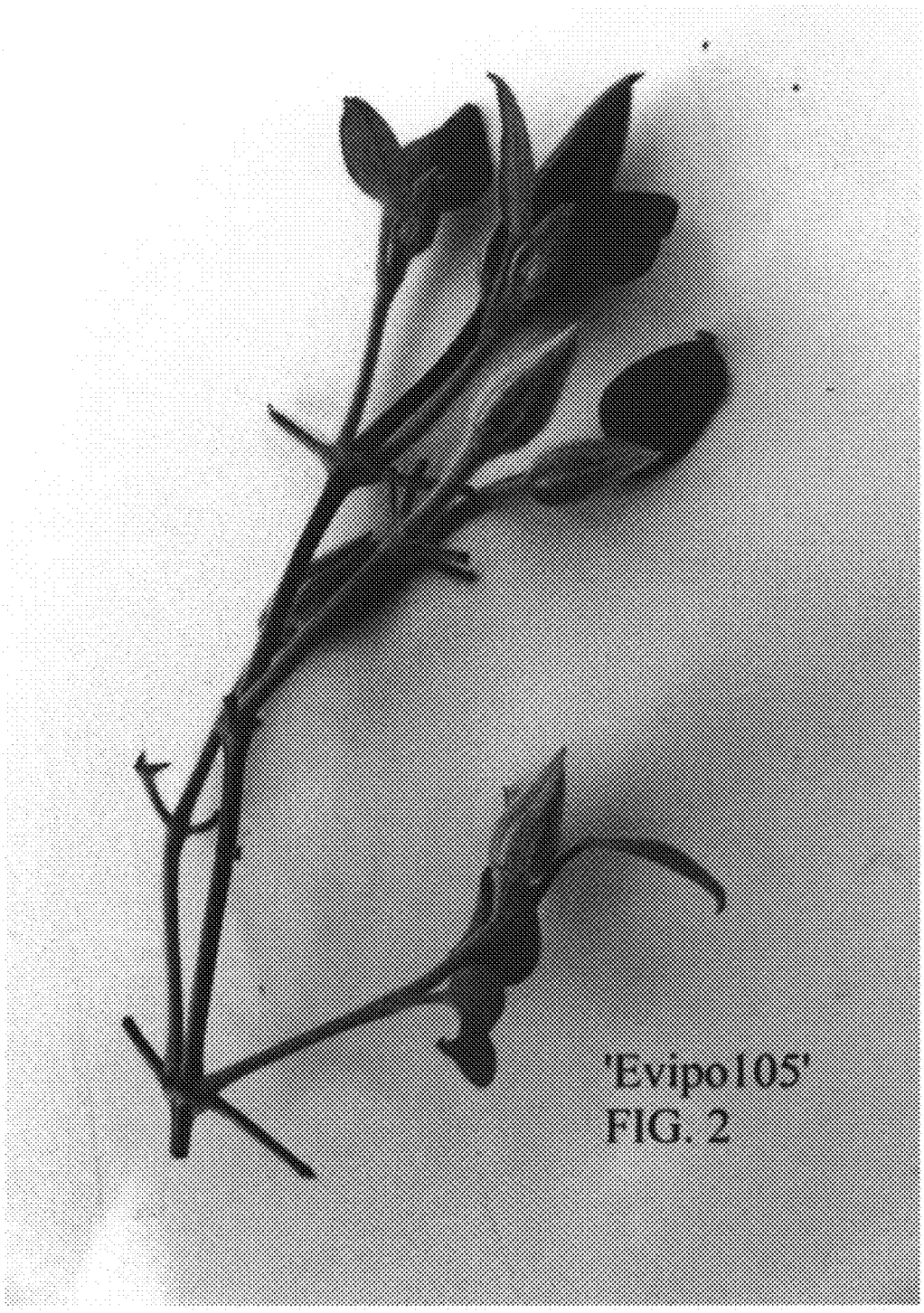
FIG. 2 shows a flowering branch with juvenile foliage and flower buds.

Illustrated plants are 2 years of age.

DETAILED DESCRIPTION OF THE VARIETY

The following is a detailed description of 'Evipo105', as observed in its growth outdoors throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo058' described and illustrated in U.S. Plant Pat. No. 28,552 are compared to 'Evipo105' in Chart 1.

CHART 1

| | 'Evipo105' | 'Evipo058' |
|---|---|---|
| Flower diameter | 110 mm | 100 mm |
| Tepal colour upper surface | Violet Group 90C with a central bar of Purple-Violet Group N82A | Purple Group 79C at the marginal zone, Purple Group N79C at the middle zone with a central bar the color of Purple Group N79B |
| Tepal count | 6 | 8 |

Flower and Flower Bud

Blooming habit: Continuous. The natural flowering period is generally from April to September.

Flower bud:

*Size.*—Normally 35 mm in length. Bud diameter is 14 mm.

*Bud form.*—Long campanulate, broad based.

*Bud color.*—Yellow-Green Group 144A with intonations of Greyed-Orange Group 177B.

*Texture.*—Pubescent.

Pedicel:

*Surface texture.*—Smooth.

*Length.*—20 to 35 mm in length with 3 mm diameter.

*Color.*—Yellow-Green Group 144A.

*Strength.*—Moderately strong.

Receptacle:

*Surface texture.*—Lightly pubescent.

*Shape.*—Broad funnel.

*Size.*—2 mm (h)×4 mm (w).

*Color.*—Yellow-Green Group 144A.

Flower arrangement:

*Location on vine.*—New growth only.

*Borne.*—Singly, or in clusters of 3 flowers.

Flower bloom:

*Size.*—On average, 110 mm diameter and 25 mm in depth.

*Profile.*—Open flowers are flat.

*Fragrance.*—None.

*Lasting quality.*—Flowers normally remain up to 14 days on the plant.

Tepals:

*Tepal color.*—The upper surface is Violet Group 90C with a central bar of Purple-Violet Group N82A. The lower surface is Violet Group N88C with central bar Greyed-White Group 156B.

*Quantity.*—Normally 6 to 8 tepals.

*Size.*—50 mm in length by 28 mm wide.

*Shape.*—Individual tepal shape is elliptic. The tepal apex is mucronate. The tepal base is typically acute.

*Apex recurvature.*—None.

*Tepal cross section.*—Flat.

*Margins.*—Entire. No undulations of margin.

*Persistence.*—Tepals drop off cleanly.

Reproductive organs:

*Pollen.*—None observed.

*Anthers.*—Size: 9 mm in length. Color: Greyed-Purple Group N186C. Quantity: On average, 50.

*Filaments.*—Color: White Group 155 N155B with intonations of Violet Group N88C at the base. Length: 10 mm.

*Pistils.*—Quantity: On average, 30.

*Stigmas.*—Inferior in location relative to the length of the filaments and the height of the anthers.

*Styles.*—Color: White Group 155A. Length: 10 mm.

Seed head characteristics: Seed not observed to date.

Plant

Plant form: Mounding.

Plant growth: Compact.

Average vigor:

Size: Seasons growth attains about 50 cm in height. Average spread is 50 cm.

Stems:

*Color.*—Juvenile stems are Yellow-Green Group 144A. Mature stems are Greyed-Orange Group N170A.

*Internodes.*—40 to 60 cm between nodes.

*Length.*—Normally 10 to 20 cm from the base of the plant to the flowering portion of the stem.

*Diameter.*—About 3 mm.

*Texture.*—Mature stems are ribbed.

Plant foliage:

*Leaf characteristics.*—Deciduous.

*Arrangement.*—Trifoliate.

*Leaf size.*—Compound leaves are about 115 mm (l)110 mm (w). Leaflets are about 55 mm (l)×30 mm (w).

*Abundance.*—On average leaves per 10 cm of stem.

*Leaf volor.*—Juvenile upper Yellow-Green Group 144A. Juvenile lower Yellow-Green Group 144A. Mature upper Yellow-Green Group 146A. Mature lower Yellow-Green Group 146B.

*Stipules.*—Absent.

*Petioles.*—Size: Normally 20 mm in length by 2 mm diameter. Texture: Smooth. Color: Yellow-Green Group 144A.

*Petioloule.*—Size: About 10 to 15 mm in length by 2 mm diameter. Texture: Smooth. Color: Yellow-Green Group 144A.

*Leaflet shape.*—Elliptic. The base is rounded, apex acute.

*Margin.*—Entire.

*Surface.*—The upper side is smooth, the lower side is smooth.

*Thickness.*—Moderate.

*Glossiness.*—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo105', substantially as described and illustrated, due to its abundant purple-violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo105'

'Evipo105'